United States Patent [19]

Fullington et al.

[11] Patent Number: 4,603,200

[45] Date of Patent: Jul. 29, 1986

[54] PROCESS FOR CONCENTRATING DILUTE SLURRIES OF CYANURIC ACID COMPOUNDS

[75] Inventors: Michael C. Fullington; Wayne H. Hammond, both of Calcasieu, La.

[73] Assignee: Olin Corporation, Cheshire, Conn.

[21] Appl. No.: 740,615

[22] Filed: Jun. 3, 1985

[51] Int. Cl.$^4$ .................. C07D 251/32; C07D 251/28
[52] U.S. Cl. ..................................... 544/190; 544/192
[58] Field of Search ............................... 544/190, 192

[56] References Cited

U.S. PATENT DOCUMENTS 3,835,136  9/1974  Hirdler et al. ...................... 260/248
3,846,424  11/1974  Hirdler et al. ...................... 260/248

OTHER PUBLICATIONS

Recent Developments in Separation Science, vol. II, pp. 205–213, Cleveland, Ohio Chemical Rubber Co., 1972.

*Primary Examiner*—John M. Ford
*Attorney, Agent, or Firm*—James B. Haglind; Thomas P. O'Day

[57] ABSTRACT

A process is described for concentrating a dilute slurry of s-triazine compounds in a liquid phase which comprises:

(a) passing said dilute slurry across an enclosed surface of a porous medium
(b) at an elevated pressure
(c) and at a flow rate of at least about 8 feet per second, whereby a portion of said liquid phase flows through said porous medium, thereby concentrating said particles in said slurry.

15 Claims, No Drawings

PROCESS FOR CONCENTRATING DILUTE SLURRIES OF CYANURIC ACID COMPOUNDS

This invention relates to a process for concentrating dilute slurries. More particularly, it relates to a process for concentrating dilute slurries of s-triazine compounds in liquid suspension.

In the preparation of trichloroisocyanuric acid and other s-triazine compounds, there is frequently a procedural step in which a solid precipitate is separated from a liquid medium. The liquid medium contains a relatively large percentage of s-triazine compounds and it must be further purified in order to recover these valuable compounds. The purified liquid medium should be sufficiently free of contaminants to permit the disposal of this liquid medium in sewers and the like.

Numerous processes have been developed to recover the s-triazine values from by-product liquid streams. For example, U.S. Pat. No. 3,835,136, which issued Sept. 10, 1974, to Louis C. Hirdler et al, and U.S. Pat. No. 3,846,424, which issued Nov. 5, 1974, to Louis C. Hirdler et al, describe processes in which the cyanuric acid values contained in aqueous solutions remaining after separating solid trichloroisocyanuric acid from the product stream is treated to recover these values. In these processes, the remaining aqueous solution of chlorinated s-triazine is reacted with a mineral acid to form chlorine and solid particles of cyanuric acid within the solution. An inert gas is used to separate the chlorine as it forms, and it is recovered for use in other parts of the process.

The chlorine-depleted aqueous slurry of solid particles of cyanuric acid is filtered or subjected to other solid-liquid separation techniques to recover the solid cyanuric acid values. The resulting solids-free mother liquor, which contains some cyanuric acid values in solution, is contacted with activated carbon which absorbs the dissolved cyanuric acid values from the mother liquor. The resulting purified mother liquor is then substantially free of contaminants and may be conveyed to conventional waste streams such as sewers, brackish water and the like. Cyanuric acid is recovered from the activated carbon by contacting the pregnant activated carbon with an aqueous solution of alkali metal hydroxide reactant, or alkali metal carbonate to form an aqueous solution of alkali metal cyanuric acid. Depending upon the concentration of alkali metal hydroxide, the alkali metal cyanurate may be in the form of mono-alkali metal cyanurate, di-alkali metal cyanurate, or tri-alkali metal cyanurate.

Cooling of this solution of alkali metal cyanurate results in precipitation of fine particles of alkali metal cyanurate. These fine particles are extremely difficult to separate from the mother liquor. When solid bowl centrifuges are used to separate the alkali metal cyanurate particles from the resulting slurry on a continuous basis, there is a substantial loss of the alkali metal cyanurate particles because of the unsettled small particles. When conventional filtration devices which utilize filter cloths, such as leaf filters, basket centrifuges and rotary drum filters, are used in an effort to recover the alkali metal cyanurate values, there is initially a substantial loss of the alkali metal cyanurate particles through the filter medium until a substantial bed of filter cake builds up on the filter medium. Because of the fine particle size of the alkali metal cyanurate, the filter cake and filter cloth then tend to blind, and the filtration rate is thereby reduced substantially. As a result, it is difficult to filter such a slurry by previously known techniques.

There is a need at the present time for an improved method for concentrating dilute slurries of solid particles of s-triazine compounds which permits substantially complete separation of the solid particles from the liquid suspending medium. Such a separation should permit disposal of the purified liquid in conventional waste disposal areas and at the same time, permits recovery of the solid alkali metal cyanurate values.

It is an object of this invention to provide an improved process for concentrating dilute slurries of s-triazine compounds.

Another object of this invention is to provide an improved process for separating alkali metal cyanurates from dilute aqueous slurries thereof.

It is a further object of this invention to provide a process for preparing purified aqueous solutions from by-product streams produced in chlorinated isocyanurate processes.

It is another object of this invention to provide an improved continuous process for preparing monosodium isocyanurate.

These and other objects of this invention are described more fully in the following detailed description of the invention.

The foregoing objects of this invention are accomplished in a process for concentrating a dilute slurry of fine particles of an s-triazine compound in a liquid phase which comprises passing said dilute slurry across an enclosed surface of a porous medium at an elevated pressure and at a flow rate of at least about 8 feet per second, whereby a portion of the liquid phase of said slurry flows through said porous medium, thereby concentrating said particles in said slurry. The clarified portion of the liquid phase passing through the porous medium is of sufficient purity to dispose of in brackish water areas or sewage disposal units.

More in detail the process of this invention is particularly suitable for concentrating dilute slurries of fine particles of s-triazine compounds in a liquid phase. Typical s-triazine compounds which can be concentrated by the process of this invention include fine particles of cyanuric acid, dichloroisocyanuric acid, trichloroisocyanuric acid, monosodium cyanurate, disodium cyanurate, trisodium cyanurate, mixtures thereof and the like. The process of this invention is preferably used in concentrating aqueous solutions of monosodium cyanurate. The description therefore will be limited to a process for concentrating aqueous solutions of monosodium cyanurate, but one skilled in the art will recognize that the same process can be employed in concentrating s-triazine compounds of the type recited above.

The particle size of the fine particles of s-triazine compounds that are concentrated in the process of this invention range from between about 0.5 and about 100, and preferably from between 1 and about 10 microns.

The concentration of fine particles of s-triazine compound in the liquid phase may range from very dilute to very concentrated slurries or suspensions. For example the solids concentration may range from about 0.1 to about 30 percent by weight of fine solids, and preferably from between about 0.5 to about 20 percent by weight of solids. The liquid suspension is generally an aqueous medium, but any other liquid in which the solid is virtually insoluble can be employed as the liquid phase of the slurry.

Concentration of the slurry of fine particles is carried out in any suitable liquid-solids separation apparatus having an enclosed porous medium in which the slurry of fine particles can be tangentially flowed over the surface of the porous medium with a sufficient velocity to sweep away at least a portion of the accumulated filter cake or layer of fine particles. For example a "cross flow" filter is very effective, in which a porous synthetic membrane is placed across a porous support medium and the slurry of fine particles flow tangentially across the surface of the membrane. The openings in the membrane range from between about 10 and about 200,000 angstroms and preferably between about 1000 and about 150,000 angstroms. The flow rate or velocity of the slurry across the membrane's surface is sufficient to sweep away at least part of the accumulated fine particle layer that may have been formed by previous filtration, leaving a portion of the membrane surface exposed to effect filtration of the fresh slurry feed. Generally the velocity of the liquid suspension is at a rate of at least about 8 feet per second, and preferably is within the range between about 12 and about 20 feet per second.

As the liquid suspension flows across the surface at this velocity, substantially all or at least a portion of the previously formed filter cake is removed from the membrane surface, and resuspended in the slurry. This slurry of resuspended particles is referred to as the "retentate" or "concentrate". The exposed membrane surface and accompanying pressure permit the flow of liquid phase or mother liquor through the pores of the membrane to a collection device.

The resuspended solids effect concentration of the slurry, which may be recycled for additional filtration. The resuspended or concentrated slurry, with or without combining with fresh slurry feed, are passed through the cross flow filter until the concentration of solids in the "retentate" reaches the desired level. For example slurries containing from about 0.1 to about 5 percent by weight of solids are fed to the cross flow filter, clarified filtrate is removed, and the concentrated slurry is recycled along with fresh slurry until all of the feed slurry has been utilized and the concentration of the final retentate is in the range from about 15 to about 30 percent by weight. However, any desirable solids concentrations may be employed.

Cross flow filtration is carried out under a pressure which ranges from between about 20 to about 100, preferably from about 30 to about 60 psig.

Ambient temperature is generally employed during filtration, in the range between about 15 and about 40, and preferably between about 20 and about 25 degrees C.

The process of this invention not only provides means for recovering an increased amount of finely divided s-triazine particles from the liquid phase, but also provides a clarified filtrate which is pure enough to release into conventional sewer systems without further treatment. Filtering the slurry of s-triazine particles in a cross flow type filter also reduces maintenance costs since the filter membrane is maintained in a substantially "unplugged" condition during operation, and shutdowns due to plugged filter medium is reduced substantially. In addition there is a reduced sensitivity to fluctuations in feed rate because of the option to recycle resuspended solids in this process.

The following examples are presented to define the invention more fully without any intention of being limited thereby. All parts and percentages are by weight unless otherwise specified.

EXAMPLES 1 and 2

The filtration system employed in Examples 1 and 2 was a cross flow filtration unit comprised of a slurry mixing tank, a pump, and four cross flow filters in series, identified as Membrane A, B, C, and D respectively. Each cross flow filter was comprised of a cylindrical housing of approximately 2" diameter and a length of about 8 feet. One or five porous cylindrical membranes having a length of about 7 feet were inserted within each filter housing. The pore size and inside diameter of each porous cylindrical membrane is set forth below in Table I.

The gap between the exterior of each porous membrane and the interior of each housing was about ⅜" when one membrane per housing was employed. When five membranes were employed there was a close fit between the exterior membrane and the interior of the housing. Piping and valve means were provided to collect the retentate of Membrane D or recycle it to the feed tank as desired. In addition piping and valve means were provided to collect filtrate from each membrane or recycle it to the feed tank.

TABLE I

| Membrane | Diameter | Wetted Area | Mean Pore Size Molecular Weight |
|---|---|---|---|
| A | ½ in. | 5.7 sq. ft. | 18,000 |
| B | ½ in. | 5.7 sq. ft. | 100,000 |
| C | 1 in. | 2.2 sq. ft. | 18,000 |
| D | 1 in. | 2.2 sq. ft. | 100,000 |

EXAMPLE 1

Dilute sodium cyanurate (NaCA) slurry (0.5%) containing NaCl (7%) was fed to the filtration unit as filtrate was removed and retentate was retained and returned to the slurry mixing tank. Fresh feed was fed to the slurry tank at the same rate filtrate was withdrawn from the filtration unit. Flow through the filtration unit was adjusted to maintain 50 psig inlet and 35 psig outlet pressure.

Filtrate pressure was maintained at atmospheric. Ultimately the feed attained 9.5% (wt/wt) NaCA concentration. The feed was then adjusted to pH 9 with sodium hydroxide and the unit was operated on total recycle (filtrate and retentate returned to feed tank). The temperature was maintained at 96°±6° F. Occasionally filtrate was removed and discarded until the feed concentration was 19.6% at day 13. Filtrate flows from each tube were measured and the filtrate was analyzed for NaCA as set forth in Table II.

TABLE II

| Membrane | Filtrate Flow | NaCA in Filtrate |
|---|---|---|
| A | 5 Gal/sq.ft/day | 0.12% |
| B | 62 Gal/sq.ft/day | 0.12% |
| C | 78 Gal/sq.ft/day | 0.12% |
| D | 83 Gal/sq.ft/day | 0.12% |

Based on a fresh feed concentration of 0.45% and 0.05% solubility, the NaCA recovered represents an 83% efficiency based on recoverable solids.

When a solid bowl centrifuge was used to filter such a dilute slurry, the recovery of solids was found to be less then about 70% efficient.

EXAMPLE 2

After cleaning the membranes in Example 1 with caustic followed by citric acid solution and water flush, they were placed back in service using the 19.6% NaCA feed slurry. The pH was adjusted to 9.0 and the pressures set at 50 and 35 psig as before. The temperature was held to 95° to 97° F. Immediately after startup the filtrate flows were measured.

| Membrane | Filtrate Flow |
| --- | --- |
| A | 164 Gal/sq. ft./day |
| B | 172 Gal/sq. ft./day |
| C | 239 Gal/sq. ft./day |
| D | 207 Gal/sq. ft./day |

After 5 days of operation on total recycle the slurry concentration had reached 20.1% NaCA through evaporation of water from the feed. Once more the filtrate flows were measured and filtrate was analyzed for NaCA.

| Membrane | Filtrate Flow | NaCA in Filtrate |
| --- | --- | --- |
| A | 117 Gal/sq.ft/day | 0.16% |
| B | 120 Gal/sq.ft/day | 0.16% |
| C | 187 Gal/sq.ft/day | 0.16% |
| D | 161 Gal/sq.ft/day | 0.16% |

Based on a fresh feed concentration of 0.45% and 0.05% solubility, the NaCA recovered represents a 73% efficiency based on recoverable solids.

What is claimed is:

1. The process for concentrating a dilute slurry of cyanuric acid compound in a liquid phase which comprises passing said dilute slurry across an enclosed surface of a porous medium, at an elevated pressure and at a flow rate of at least about 8 feet per second, whereby a portion of said liquid phase flows through said porous medium, thereby concentrating said particles in said slurry.

2. The process of claim 1 wherein cyanuric acid compound is selected from the group consisting of cyanuric acid, dichlorocyanuric acid, trichlorocyanuric acid, monosodium cyanurate, disodium cyanurate, trisodium cyanurate and mixtures thereof.

3. The process of claim 2 wherein said porous medium has openings in the range from between about 10 and about 200,000 angstroms.

4. The process of claim 2 wherein said porous medium has openings in the range from between about 1,000 and about 150,000 angstroms.

5. The process of claim 4 wherein said porous medium has a cylindrical surface.

6. The process of claim 3 wherein said elevated pressure is in the range from between about 20 and about 100 psig.

7. The process of claim 5 wherein said pressure is in the range from between about 60 and about 30 psig.

8. The process of claim 7 wherein the flow rate of said slurry is in the range from between about 8 and about 20 feet per second.

9. The process of claim 8 wherein the flow rate of said slurry is in the range from between about 12 and about 20 feet per second.

10. The process of claim 3 wherein said dilute slurry has a concentration of fine particles in the range from between about 0.1 and about 30 percent by weight.

11. The process of claim 9 wherein said dilute slurry has a concentration of fine particles in the range from between about 0.5 and about 20 percent by weight.

12. The process of claim 3 wherein the particle size of said cyanuric acid compound is in the range between about 0.5 and about 100 microns.

13. The process of claim 11 wherein the particle size of said cyanuric acid compound is in the range between about 1 and about 10 microns.

14. The process of claim 12 wherein said dilute slurry is an aqueous slurry of monosodium cyanurate.

15. The process of claim 13 wherein said dilute slurry is an aqueous slurry of monosodium cyanurate.

* * * * *